United States Patent
Onishi et al.

(10) Patent No.: US 9,409,145 B2
(45) Date of Patent: Aug. 9, 2016

(54) SEPARATING AGENT

(71) Applicant: Daicel Corporation, Osaka-shi, Osaka (JP)

(72) Inventors: Takafumi Onishi, Himeji (JP); Yasuto Morishita, Himeji (JP); Masahiro Miyamoto, Himeji (JP)

(73) Assignee: DAICEL CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 14/648,546

(22) PCT Filed: Nov. 29, 2013

(86) PCT No.: PCT/JP2013/082215
§ 371 (c)(1),
(2) Date: May 29, 2015

(87) PCT Pub. No.: WO2014/087937
PCT Pub. Date: Jun. 12, 2014

(65) Prior Publication Data
US 2015/0343420 A1    Dec. 3, 2015

(30) Foreign Application Priority Data
Dec. 6, 2012 (JP) .................................. 2012-267017

(51) Int. Cl.
| | | |
|---|---|---|
| B01J 20/26 | (2006.01) | |
| B01J 20/28 | (2006.01) | |
| B01J 20/286 | (2006.01) | |
| B01J 20/32 | (2006.01) | |
| B01J 20/22 | (2006.01) | |
| B01J 20/24 | (2006.01) | |
| B01J 20/281 | (2006.01) | |
| C07B 57/00 | (2006.01) | |
| C07K 17/04 | (2006.01) | |
| C08G 81/00 | (2006.01) | |
| C12N 15/09 | (2006.01) | |
| G01N 30/88 | (2006.01) | |
| C09D 183/02 | (2006.01) | |
| C07K 1/22 | (2006.01) | |
| C12N 15/10 | (2006.01) | |

(52) U.S. Cl.
CPC ............ *B01J 20/28016* (2013.01); *B01J 20/22* (2013.01); *B01J 20/24* (2013.01); *B01J 20/26* (2013.01); *B01J 20/265* (2013.01); *B01J 20/281* (2013.01); *B01J 20/286* (2013.01); *B01J 20/3204* (2013.01); *B01J 20/3255* (2013.01); *B01J 20/3272* (2013.01); *B01J 20/3274* (2013.01); *C07B 57/00* (2013.01); *C07K 17/04* (2013.01); *C08G 81/00* (2013.01); *C09D 183/02* (2013.01); *C12N 15/09* (2013.01); *G01N 30/88* (2013.01); *C07K 1/22* (2013.01); *C12N 15/1006* (2013.01); *G01N 2030/8877* (2013.01)

(58) Field of Classification Search
CPC .......................................................... B01J 20/26
USPC .......................................................... 502/402
See application file for complete search history.

(56) References Cited

U.S. PATENT DOCUMENTS

| | | |
|---|---|---|
| 3,922,392 A | 11/1975 | Kohlschütter et al. |
| 4,512,898 A | 4/1985 | Oi et al. |
| 5,679,572 A | 10/1997 | Okamoto et al. |
| 2003/0186298 A1 | 10/2003 | Nishimura et al. |
| 2004/0077812 A1 | 4/2004 | Okamoto et al. |
| 2005/0181441 A1 | 8/2005 | Nishimura et al. |
| 2007/0189944 A1 | 8/2007 | Kirkland et al. |
| 2010/0041878 A1 | 2/2010 | Ohnishi et al. |
| 2011/0226990 A1 | 9/2011 | Glennon et al. |
| 2013/0204014 A1 | 8/2013 | Nishihara et al. |

FOREIGN PATENT DOCUMENTS

| | | |
|---|---|---|
| CN | 1280986 A | 1/2001 |
| EP | 2 853 892 A1 | 4/2015 |
| JP | 49-036396 | 4/1974 |
| JP | 07-138301 A | 5/1995 |
| JP | 10-128089 A | 5/1998 |
| JP | 11-335306 A | 12/1999 |
| JP | 2002-148247 A | 5/2002 |
| JP | 2003-284552 A | 10/2003 |
| JP | 2003-327675 A | 11/2003 |
| JP | 2009-091535 A | 4/2009 |
| JP | 2010-077022 A | 4/2010 |
| JP | 2012-018135 A | 1/2012 |
| JP | 2012-509974 A | 4/2012 |
| WO | WO 02/088204 A1 | 11/2002 |
| WO | WO 2008/102920 A1 | 8/2008 |
| WO | WO 2011/136721 A1 | 11/2011 |
| WO | WO 2012/050124 A1 | 4/2012 |

OTHER PUBLICATIONS

Office Action of Chinese Patent Office issued in Application No. 201380063640.0 with English translation dated Dec. 25, 2015 (23 pages).

Shoji Hara and Akira Dobashi, "Liquid Chromatographic Resolution of Enantiomers on Normal-Phase Chiral Amide-Bonded Silica Gel: Retentions of Optically Active α-Amino Acid Derivatives on N-Acyl Homologues of L-Valylaminopropylsilanized Silica Phases" Journal of Chromatography, 186(1979), pp. 543-552.

(Continued)

Primary Examiner — Edward Johnson
(74) Attorney, Agent, or Firm — Flynn, Thiel, Boutell & Tanis, P.C.

(57) ABSTRACT

Provided is a separating agent comprising a carrier and a ligand fixed on a surface of a carrier by chemical bonding, in which the carrier is a core-shell particle formed of a non-porous core and a porous shell, the shell having a pore diameter of 9 nm or more and formed of a hydrolysate of polyalkoxysiloxane, and the ligand is an optically active polymer, optically inactive polyester, protein, nucleic acid, or optically active organic compound with a molecular weight of 50 to 1000.

8 Claims, No Drawings

(56) References Cited

OTHER PUBLICATIONS

English translation of the International Preliminary Report on Patentability and Written Opinion of the International Searching Authority (8 pages).
European Patent Office Search Report dated Aug. 4, 2015 (10 pages).
International Search Report for PCT/JP2013/082215 (3 pgs.).
*Comparative high-performance liquid chromatography enantioseparations on polysaccharide based chiral stationary phases prepared by coating totally porous and core-shell silica particles*, by K. Lomsadze et al, Journal of Chromatography A, vol. 1234, 2012, pp. 50-55.
*Controlled Chiral Recognition of Cellulose Triphenylcarbamate Derivatives Supported on Silica Gel*, by Y. Okamoto et al, Journal of Chromatography, vol. 363, 1986, pp. 173-186.

SEPARATING AGENT

TECHNICAL FIELD

The present invention relates to a separating agent comprising a specific carrier and a specific ligand fixed on the surface of the carrier by chemical bonding.

BACKGROUND ART

In the industrial fields related to medicines, agrochemicals, and biochemicals, it is an extremely important problem to separate/purify a target substance to be produced, and methods using separating agents have been conventionally employed as techniques for such separation. Examples of principles on which a substance to be separated is separated using such separating agents include one in which affinity between a separating agent and a target substance is utilized, and one in which the optical activity of both a separating agent and a target substance is utilized.

Separating agents, in which wholly porous silica gel is used as a carrier and various ligands are fixed to the carrier in accordance with a target substance to be separated, are conventionally known as such separating agents.

Known as such a separating agent obtained using wholly porous silica gel as a carrier is, for example, a separating agent conaining an optically active polymer fixed therein. In the case of using such a separating agent in which an optically active polymer is fixed to a carrier, optical resolution can be performed.

Having been reported as the optically active polymer are polysaccharide derivatives derived from polysaccharides such as cellulose (see, for example, patent document 1), optically active poly(meth)acrylamides (see, for example, patent document 2), optically active poly(amino acid)s (see, for example, patent document 3), and optically active polyamides (see, for example, patent documents 4 and 5).

Meanwhile, a separating agent for optical isomers is also known in which an optically active low-molecular-weight compound (e.g., a compound having a binaphthyl structure or crown ether structure) is bonded to a carrier by chemical bonding (see, for example, patent document 6).

Furthermore reported is a separating agent which contains, as a carrier, particles constituted of a synthetic polymer having a crosslinked structure and further contains, as a ligand fixed thereto, either a protein or a glycoprotein having a sugar chain (see, for example, patent document 7).

With respect to separating agents obtained by fixing a nucleic acid to a carrier, a technique in which DNA is immobilized to a glass substrate through chitosan is, for example, known (see, for example, patent document 8).

Moreover, with respect to chips for use in identifying ionic polymers, a technique in which DNA, RNA, or the like is fixed to a carrier such as glass is also known (see, for example, patent document 9).

Wholly porous silica gel has conventionally been used as a carrier to be used for fixing ligands thereto. Regarding this, also known besides such wholly porous particles are core/shell particles each including a non-porous core and a porous shell covering the outer surface thereof (see, for example, patent document 10). Also known is a separating agent for optical isomers which is obtained by fixing cellulose tris(4-chloro-3-methylphenylcarbamate) to such core-shell particle which have a pore diameter of 10 nm (for example, non-patent document 1).

Patent Document 1: WO 2008/102920
Patent Document 2: WO 02/088204
Patent Document 3: Japanese Patent Application Laid-open No. H10-128089
Patent Document 4: Japanese Patent Application Laid-open No. H11-335306
Patent Document 5: Japanese Patent Application Laid-open No. 2009-91535
Patent Document 6: Japanese Patent Application Laid-open No. 2003-327675
Patent Document 7: Japanese Patent Application Laid-open No. 2012-18135
Patent Document 8: Japanese Patent Application Laid-open No. 2010-77022
Patent Document 9: Japanese Patent Application Laid-open No. 2003-284552
Patent Document 10: Japanese Patent Application Laid-open No. S49-36396
Patent Document 11: Japanese Patent Application Laid-open No. H7-138301
Patent Document 12: WO 2012/050124
Non-patent document 1: J. Chromatogr. A 1234, 50-55 (2012)
Non-patent document 2: J. Chromatogr. 363, 173 (1986)

DISCLOSURE OF THE INVENTION

The present invention provides a novel separating agent obtained using a core-shell particle as a carrier, by fixing various ligands on this carrier by chemical bonding.

The inventors have discovered that a separating agent obtained by using a core-shell type particle consisting of a non-porous core and a porous shell instead of a completely porous particle (such as conventional silica gel) as the carrier of the separating agent, and fixing various ligands thereon, is useful for separating various target substances.

That is, the present invention provides a separating agent comprising a carrier and a ligand fixed on a surface of the carrier by chemical bonding, wherein the carrier is a core-shell particle formed of a non-porous core and a porous shell, the shell having a pore diameter of 9 nm or more and formed of a hydrolysate of polyalkoxysiloxane, and the ligand is an optically active polymer, optically inactive polyester, protein or nucleic acid.

MODE FOR CARRYING OUT THE INVENTION

Core-Shell Particle

A core-shell particle having a non-porous core with a porous shell on the outer surface of the core is used in the separating agent of the present invention. The pore diameter of the surface of the core-shell particle is 9 nm or more.

It is expected that giving the core-shell particle a pore diameter of 9 nm or more will contribute to good separation of target substances because the specific surface area is greater and more ligands can be introduced. The pore diameter is normally 100 nm or less.

The pore diameter of the core-shell particle can be measured by the mercury intrusion technique.

The mercury intrusion technique is a method in which pressure is applied to cause intrusion of mercury into an opening, and the pore diameter of an idealized cylindrical pore is calculated from Washburn's equation using the pressure value and the corresponding introduced mercury volume. The standards of JIS R1655, which was established for ceramic molded bodies, are applicable to this technique.

The term "nonporous" used herein means that when the specific surface area ($m^2/g$) of the surface of the core particles determined by the BET method is expressed by A and the surface area (m²/g) thereof per unit weight that can be calculated from the surface area ($4\pi r^2$, which is calculated from the particle radius r) determined from the particle diameter of the core particles is expressed by B, then the value of (A−B)/B× 100 is less than 20.

Meanwhile, the term "porous" used herein means that the specific surface area of the surface of the material, determined by the BET method, is 10 mm²/g or larger.

The thickness ratio of the cores to the shells of the core-shell particle is usually from 1:9 to 9:1. This ratio is preferably from 4:1 to 2:1 from the standpoint of ensuring the satisfactory property of separating a target substance. This ratio can be controlled by controlling the thickness of the shell layers of the core-shell particle as will be described later.

The term "thickness of a core" herein means the diameter of the core.

The material of the core as a constituent component of the core-shell particle is an inorganic substance. Specific examples thereof include non-porous particles selected from materials represented by glasses, metals such as titanium and zirconium, oxides of these metals, and clay minerals such as bentonite and mica.

The particle used as the material of this core preferably has a particle size of at least 0.1 μm, or more preferably at least 0.5 μm, or especially at least 1 μm. Moreover, the particle size of the particle used as the material of this core is preferably 200 μm or less, or more preferably 100 μm or less, or still more preferably 50 μm or less.

The particle size of the core-shell particle is normally at least 0.2 μm and no more than 1000 μm. In the present invention, the particle size of the core-shell particle is a particle size measured by a mean particle size measurement method using centrifugal sedimentation.

The material of the shell as a constituent component of the core-shell particle is obtained by partially hydrolyzing an alkoxysilane and further hydrolyzing the resultant polyalkoxysiloxane. Such material is preferred from the standpoint that the core-shell particle can be easily produced.

Preferred as the alkoxysilane are tetraalkoxysilanes. Preferred of these are tetramethoxylane, tetraethoxysilane, tetrapropoxysilane, and tetrabutoxysilane. Use of tetraethoxysilane is more preferred.

For production of the core-shell particle, Japanese Patent Application Laid-open No. S49-36396 can be referred to. Specifically, an alkoxysilane is first partially hydrolyzed to yield a polyalkoxysiloxane. The polyalkoxysiloxane thus obtained is dissolved in a solvent such as an ether, acetone, or dichloromethane to prepare a polyalkoxysiloxane solution. This solution is applied to particles serving as the cores, or the core particles are immersed in this solution. Thereafter, the solvent is removed to deposit a layer of the polyalkoxysiloxane as shells on the surface of the core particles. Subsequently, the deposited polyalkoxysiloxane is condensation-polymerized (hydrolyzed) in the presence of water. Thus, core-shell particle can be obtained.

The thickness of the shell as a constituent component of the core-shell particle can be controlled, as appropriate, in the range of 0.1 to 100 μm. An example of methods therefor is to regulate the viscosity of the alkoxysilane which becomes the shell. For example, in cases when shell having an increased thickness is to be formed, the viscosity of the alkoxysilane is lowered.

Examples of methods for controlling the specific surface area and pore diameter of the shell include a method in which the pH of the aqueous solution to be used when deposited shell is condensation-polymerized is regulated. For example, the pH of the aqueous solution is increased when a larger specific surface area and a larger pore diameter are to be obtained.

The term "thickness of a shell" herein means the value obtained by subtracting the diameter of the core from the diameter of the core-shell particle and dividing the obtained value by 2.

A commercially available "core-shell silica gel" may also be used for this core-shell particle. Such a commercial product has a pore diameter, specific surface area and particle size within the aforementioned ranges as catalog values. In the case of a commercial core-shell silica gel, it is possible to use a product in which the core consists of glass and the shell consists of silica gel (polyalkoxysiloxane hydrolysate).

The core-shell particle used as the carrier of the separating agent of the present invention may also be subjected to surface treatment. Examples of methods of surface treatment include methods using 3-aminopropyl triethoxysilane and other silane coupling agents having amino groups.

The amino groups introduced by such surface treatment may be used as reactive groups when performing chemical bonding with the ligands discussed below.

<Ligand>

The term "ligand" used herein means a substance which is fixed to the core-shell particle serving as the carrier and which shows a physical affinity for the target substance to be separated or is capable of recognizing the asymmetry thereof.

1. Optically Active Polymer

Examples of the ligand usable in the separating agent of the invention contain optically active polymers. The term "optically active polymer" used herein means a polymer, a solution of which, when plane-polarized light is passed therethrough, has optical rotary activity that rotates the plane of polarization, i.e., chirality.

More specifically, the optically active polymer is obtained from a monomer having optical activity, or is obtained by polymerizing an optically inactive monomer using a polymerization catalyst which is optically active. The polymer has a molecular weight of 1,000 to 1,000,000.

1-(1) Polysaccharides or Derivatives Thereof

Examples of the optically active polymer serving as the ligand for use in the invention include polysaccharides or derivatives thereof. Examples of such polysaccharides include β-1,4-glucan (cellulose), α-1,4-glucan (amylose, amylopectin), α-1,6-glucan (dextran), β-1,6-glucan (pustulan), β-1,3-glucan (curdlan, schizophyllan), α-1,3-glucan, β-1,2-glucan (crown-gall polysaccharide), β-1,4-galactan, β-1,4-mannan, α-1,6-mannan, β-1,2-fructan (inulin), β-2,6-fractan (levan), β-1,4-xylan, β-1,3-xylan, β-1,4-chitosan, β-1,4-N-acetylchitosan (chitin), pullulan, agarose, alginic acid, α-cyclodextrin, β-cyclodextrin, γ-cyclodextrin, nigeran, and starch containing amylose.

Preferred of these are cellulose, amylose, β-1,4-chitosan, chitin, β-1,4-mannan, β-1,4-xylan, inulin, curdlan, pullulan, α-cyclodextrin, β-cyclodextrin, γ-cyclodextrin, nigeran, and the like, from which high-purity polysaccharides can be easily obtained. More preferred are cellulose, amylose, pullulan, and nigeran.

The number-average degree of polymerization (the average number of pyranose or furanose rings contained in one molecule) of each polysaccharide is preferably 5 or greater, more preferably 10 or greater. Although there is no particular upper limitation thereon, the number-average degree of polymerization thereof is preferably 1,000 or less from the standpoint of ease of handling, and is more preferably 5 to 1,000, even more preferably 10 to 1,000, especially preferably 10 to 500.

With respect to these polysaccharides, an ester derivative, carbamate derivative, or the like obtained by chemically modifying, for example, cellulose or amylose can be used as the ligand according to the invention.

Such polysaccharide derivatives are known to have a high optical resolution ability when used as a chiral fixing phase.

Specific examples of the ester derivative and carbamate derivative include the cellulose derivative described in Japanese Examined Patent Publication No. H4-42371, in which hydroxy groups of cellulose have been modified with a substituent formed by replacing part of the hydrogen atoms of the aromatic ring of phenyl carbamate with a halogen (fluorine or chlorine), and the cellulose derivative and amylose derivative described in Japanese Patent Application Laid-open No. 2005-315668, in which hydroxy groups of cellulose or amylose have been modified with a substituent formed by replacing part of the hydrogen atoms of the aromatic ring of phenyl carbamate with one or more fluorine atoms, alkyl groups, or alkoxy groups. These derivatives also are usable as the ligand according to the invention.

Examples of the substituent with which hydrogen atom(s) of the aromatic ring of such phenyl carbamate derivatives are replaced include a halogen alone, a combination of a halogen and an alkyl group, and an alkyl group alone. Preferred examples of the halogen in such case include chlorine. Examples of the alkyl group include ones having 1-3 carbon atoms, and methyl is especially preferred of these.

Of the above polysaccharides or derivatives thereof, it is especially preferred to use a polysaccharide derivative selected from those described above, from the standpoints of the ability to separate an optical isomer to be separated and of ease of fixation thereof to the core-shell particle.

Of the aforementioned polysaccharides and derivatives thereof, a polysaccharide derivative is especially desirable from the standpoint of ability to separate an optical isomer that is the object of separation, and because it is easier to fix on the core-shell particle.

The polysaccharide derivative is not limited to the aforementioned, and an appropriate one may be used.

Means of fixing the polysaccharide or derivative thereof on the core-shell particle by chemical bonding include chemical bonding between the core-shell particle and the polysaccharide derivative, chemical bonding using a third component, reactions caused by light irradiation of the polysaccharide derivative on the carrier, exposure to gamma rays or other radiation, or exposure to microwaves or other electromagnetic waves, and chemical bonding by radical reactions using radical initiators.

For example, chemical bonding between the core-shell particle and the polysaccharide derivative can be accomplished by a method such as that described in Japanese Patent Application Publication No. H07-138301 (hereunder called a reducing amination method), in which a reducing terminal of a polysaccharide having a reducing terminal is chemically bonded with a surface treated carrier by a method of reducing the reducing terminal with a reducing agent after formation of a Schiff base between an aldehyde group and an amino group for example, to produce a secondary amine (Elisabeth Kallin et al., Glycoconjugate J (1986) 3, 311-319), after which the polysaccharide is derivatized to obtain a target packing material for separation of optical isomers.

Chemical bonding of a polysaccharide derivative on a core-shell particle using a third component can be accomplished by a method such as that described in the examples of Japanese Patent Application Publication No. 2002-148247, in which a polymerizable polysaccharide derivative with an introduced vinyl or other polymerizable group and a core-shell particle also with an introduced vinyl or other polymerizable group are co-polymerized in the presence of a third component (polymerizable monomer) having a vinyl group or the like.

Chemical bonding by light irradiation of a core-shell particle and a polysaccharide derivative can be accomplished by a method such as that described in Japanese Translation of PCT Application No. H11-510193, in which a polysaccharide derivative is first fixed by coating it on a core-shell particle, and this is then exposed to light from an immersive mercury lamp to thereby optically crosslink the polysaccharide derivative.

Chemical bonding by exposing a polysaccharide derivative coated on a core-shell particle to gamma rays or other radiation or microwaves or other electromagnetic waves can be accomplished by a method such as that described in Japanese Patent Application Publication No. 2004-167343, in which a polysaccharide derivative is first coated on a surface-treated core-shell particle, and then exposed to gamma rays to thereby chemically bond the polysaccharide derivative.

In addition, chemical bonding between a core-shell particle and a polysaccharide derivative can be accomplished for example by a method in which a polysaccharide derivative having alkoxysilyl groups introduced into some of the hydroxyl groups or amino groups of the polysaccharide derivative is coated on a core-shell particle, and cross-links are formed from the alkoxysilyl groups in a suitable solvent to thereby chemically bond the polysaccharide derivative.

The amount of the polysaccharide or derivative thereof that is fixed on the core-shell particle is preferably 1.0 to 25 parts by weight per 100 parts by weight of the core-shell particle.

1-(2) Poly(meth)acrylamides

In the invention, examples of the optically active polymer serving as the ligand include poly(meth)acrylamides. Among such poly(meth)acrylamides, poly(meth)acrylamide obtained by polymerizing a (meth)acrylamide which is represented by the following formula (I) and is optically active can be preferably used.

Examples of such polymerization reaction include radical polymerization in which a free-radical polymerization initiator such as AIBN (azobisisobutyronitrile) is used in the presence of a Lewis acid catalyst.

The Lewis acid used therein is desirably a metallic Lewis acid which is a metal salt (MX). Examples thereof include scandium triflate, yttrium triflate, magnesium bromide, hafnium chloride, ytterbium triflate, and lutetium triflate.

In the polymerization reaction, when (meth)acrylamide is liquid at normal temperature and normal pressure, it can be polymerized even under solvent-free conditions. In cases when the (meth)acrylamide is solid, any common organic solvent which has no radical-trapping effect can be used as a reaction solvent. More desirable are tetrahydrofuran, chloroform, methanol, and the like.

Other polymerization conditions can be controlled, as appropriate, with reference to WO 02/088204.

[C1]

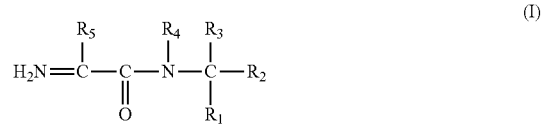

(I)

(In the formula, $R_1$, $R_2$, and $R_3$ are different and each represent a hydrogen atom, a monovalent hydrocarbon group having 1-30 carbon atoms, or a monovalent group of atoms including a heteroatom; $R_4$ represents a hydrogen atom or a monovalent hydrocarbon group having 1-30 carbon atoms; and $R_5$ represents a hydrogen atom or a methyl group.)

It is preferable that $R_1$, $R_2$, and $R_3$ be different and each be a hydrogen atom, alkyl group having 1-6 carbon atoms, aryl group, aralkyl group, carboalkoxy group, carbamoyl group, aminoalkyl group, amino group, alkoxyalkyl group, alkoxy group, or silyl group, and that $R_4$ be a hydrogen atom, alkyl group having 1-6 carbon atoms, aryl group, or aralkyl group. It is especially preferable that $R_4$ be a hydrogen atom.

The fixed amount of the poly(meth)acrylic acid amide on the core-shell particle is preferably 1.0 to 25 parts by weight per 100 parts by weight of the core-shell particle.

As one method of fixing the poly(meth)acrylic acid amide by chemical bonding on the core-shell particle, reactive functional groups can be bonded to the core-shell particle, and either these reactive functional groups can be reacted with the amide groups of the poly(meth)acrylic acid amide, or else functional groups capable of reacting with these reactive functional groups can be introduced into the poly(meth)acrylic acid amide and reacted to bond them with the amide.

Specifically, one example is a method in which the core-shell particle is provided with epoxy groups by surface treatment with a silane coupling agent or the like containing epoxy groups, and these epoxy groups are reacted with the amide groups of the poly(meth)acrylic acid amide.

In another method, polymerizable functional groups are introduced into the core-shell particle by surface treatment with a silane coupling agent or the like containing vinyl groups, (meth)acryloyl groups or other polymerizable functional groups, while meanwhile polymerizable functional groups such as (meth)acryloyl groups are also introduced into the poly(meth)acrylic acid amide using an isocyanic acid ester as described in Japanese Patent Application Publication No. 2006-177795, and the polymerizable functional groups are reacted with each other to cause chemical bonding by co-polymerization.

1-(3) Poly(amino Acid)s

Examples of the optically active polymer for use in the invention include poly(amino acid)s. The term "poly(amino acid)s" used herein is not included in the proteins which will be described later. Examples of such poly(amino acid)s include ones represented by the following formula (II). Such poly(amino acid)s can be synthesized, for example, by the method described in Japanese Patent Application Laid-open No. S60-193538.

[C2]

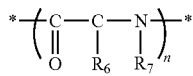

(II)

In formula (II), n is 5 or greater, and $R_6$ is a group selected from alkyl groups having 1-5 carbon atoms, a phenyl group, aralkyl groups having 7-12 carbon atoms, and heterocyclic groups. These groups may have a substituent such as a hydroxyl group, carboxyl group, mercapto group, amino group, or methylthio group. $R_7$ is an alkyl group having 1-5 carbon atoms, and is preferably a methyl or ethyl group.

Examples of heterocycles constituting the heterocyclic groups include 5-pyrazolone, pyrazole, triazole, oxazolone, isooxazolone, barbituric acid, pyridone, pyridine, rhodanine, pyrazolydinedione, pyrazolopyridone, Meldrum's acid, and fused heterocycles each including any of these heterocycles and, fused thereto, an aromatic hydrocarbon ring or a heterocycle.

Examples of α-aminocarboxylic acids for constituting such poly(amino acid)s include alanine, valine, leucine, phenylalanine, proline, glutamic acid, and aspartic acid. Examples of constituent materials for the poly(amino acid)s further include amino acid derivatives such as benzyl aspartate, methyl glutamate, benzyl glutamate, carbobenzoxylysine, carbobenzoxyornithine, acetyltyrosine, and benzylserine.

In formula (II), n is preferably 100 or less, more preferably 10 to 40.

In Formula (II) above, n is preferably 100 or less, and is more preferably 10 to 40.

The fixed amount of the polyamino acid relative to the core-shell particle is preferably 1.0 to 25 parts by weight per 100 parts by weight of the core-shell particle.

As one method of fixing the polyamino acid by chemical bonding on the core-shell particle, reactive functional groups can be bonded to the core shell particle, and either these reactive functional groups can be reacted with the amino groups of the polyamino acid, or else functional groups capable of reacting with these reactive functional groups can be introduced into the polyamino acid and reacted to bond them with the core-shell particle.

One method is to introduce epoxy groups that react with the amino groups of the polyamino acid as the reactive functional groups introduced into the core-shell particle. One specific method is to surface treat the core-shell particle with a silane coupling agent containing epoxy groups.

Another method is to first introduce polymerizable functional groups into the core-shell particle by surface treatment with a silane coupling agent or the like containing vinyl groups, (meth)acryloyl groups or other polymerizable functional groups, while also reacting the polyamino acid with a monomer (such as chloride acrylate, glycidyl methacrylate or chloromethyl styrene) having polymerizable functional groups capable of reacting with the amino groups of the polyamino acid to thereby synthesize a polyamino acid having introduced vinyl or other polymerizable functional groups at the termini, and then to react the polymerizable functional groups of the core-shell particle with the polymerizable functional groups of the polyamino acid to thereby form chemical bonds by co-polymerization.

1-(4) Polyamides

Examples of the optically active polymer for use in the separating agent of the invention include polyamides. The polyamide has one optically active amino acid residue in the main chain of each repeating unit.

As monomer ingredients for synthesizing the optically active polyamide, an N-substituted amino acid which is an optically active dicarboxylic acid and a diamine were adopted. As the N-substituted amino acid, use can be made of, for example, an N-substituted glutamic acid or an N-substituted aspartic acid. As the diamine, use can be made of an aromatic diamine such as 4,4'-diaminodiphenylmethane or 1,3-phenylenediamine.

One example of methods for synthesizing the polyamide is explained. The polyamide can be synthesized, as stated above, by polymerizing an N-substituted amino acid which is an optically active dicarboxylic acid with a diamine. Specifically, N-methylpyrrolidone (hereinafter, abbreviated to "NMP") is mixed with pyridine (hereinafter, abbreviated to "Py") in a volume ratio of, for example, 4:1. To the resultant liquid is added lithium chloride (hereinafter, abbreviated to "LiCl") in an amount of, for example, 4 wt %. To, for example, 7.5 cm³ of the resultant liquid (hereinafter, referred to as "NMP-Py mixture solution") are added a given amount, for example, 3 mmol, of benzoyl-L-glutamic acid (N-substituted amino acid which is an optically active dicarboxylic acid), an amount equimolar therewith, for example, 3 mmol, of 4,4'-diaminodiphenylmethane (diamine), and a molar amount which is twice the amount of each, for example, 6 mmol, of triphenyl phosphite. The mixture is heated with stirring at a given temperature, e.g., 80° C. for a given period, e.g., 3 hours. After completion of the reaction, the reaction product is added dropwise to methanol, and the resultant mixture is filtered to obtain a polymer, which is vacuum-dried.

Methods for synthesizing the polyamides according to the invention are not limited to the methods described above, and the polyamides may be synthesized by any method other than those. The suitable reaction temperature and reaction time vary depending on reagents used in the reaction and the amounts thereof. The reaction time, reaction temperature, and reagent amounts shown above are examples of conditions under which the optically active polymer according to the invention can be obtained, and can be modified as appropriate.

Because the polyamides of the present invention are synthesized using an N-substituted amino acid, which is an optically active dicarboxylic acid, it has a D- or L-optically active substance recognition site within the polymer, and this optically active substance recognition site can be used to perform optical resolution.

The fixed amount of the polyamide relative to the core-shell particle is preferably 1.0 to 25 parts by weight per 100 parts by weight of the core-shell particle.

One method of fixing the polyamides by chemical bonding on the core-shell particle is to bond reactive functional groups to the core-shell particle, and either bond these reactive functional groups to the amide groups of the polyamide, or else introduce functional groups capable of reacting with these reactive functional groups into the polyamide, and react them to bond the polyamide.

Specifically, one example is a method in which the core-shell particle is provided with epoxy groups by surface treatment with a silane coupling agent or the like having epoxy groups, and these epoxy groups are reacted with the amide groups of the polyamide.

In another method, polymerizable functional groups are introduced into the core-shell particle by surface treatment with a silane coupling agent containing vinyl groups, (meth) acryloyl groups or other polymerizable functional groups, while meanwhile polymerizable functional groups such as (meth)acryloyl groups are also introduced into the polyamide using an isocyanic acid ester as described in Japanese Patent Application Publication No. 2006-177795, and the polymerizable functional groups are reacted with each other to cause chemical bonding by co-polymerization.

2. Optically Inactive Polyester

Examples of the ligand for use in the invention include an optically inactive polyester. Examples of such polyester include, as polyester, poly(ethylene terephthalate), poly(butylene terephthalate), polyethylene/poly(butylene terephthalate), poly(trimethylene terephthalate), poly(ethylene naphthalate), poly(butylene naphthalate), poly(lactic acid), poly (glycolic acid), poly(ε-caprolactone), and poly(oxycarbonyloxy-1,4-phenylene/2,2-isopropylidene-1,4-phenylene) (polycarbonate of bisphenol A). It is preferred to use poly(ethylene terephthalate), poly(butylene terephthalate), poly(lactic acid), or poly(glycolic acid) thereamong.

The weight-average molecular weight of such a polyester is preferably 10,000 to 1,000,000, more preferably 20,000 to 200,000, from the standpoints of tenacious physical adsorption onto the carrier and ease of handling due to an increase in the viscosity of a solvent for polymer dissolution.

The weight-average molecular weight of this polyester is preferably 10000 to 1000000 or more preferably 20000 to 200000 to facilitate handling by increasing the viscosity of the polymer-dissolving solvent.

One way of fixing the polyester by chemical bonding on the core-shell particle is to bond reactive functional groups to the core-shell particle, introduce functional groups capable of reacting with these reactive functional groups into the polyester, and react them to bond the polyester.

Specifically, one example is a method in which functional groups that form covalent bonds with epoxy and other amino groups are introduced into the core-shell particle by surface treatment with a silane coupling agent or the like having epoxy groups, while the polyester is chemically treated with a polyamine to introduce amino groups into the polyester.

Polyamines include $C_{2-8}$ (poly)alkylene polyamines, and examples are ethylene diamine, propylene diamine, butyrene diamine, diethylene triamine, triethylene tetramine, tetraethylene pentamine and the like.

Of these polyamines, ethylene diamine, diethylene triamine, triethylene tetramine and tetraethylene pentamine are desirable, and diethylene triamine is especially desirable. In particular, using a polyamine containing at least three amino groups is desirable for introducing amino groups into the polyester. Moreover, a low-molecular-weight amine is desirable for ease of removal after chemical treatment.

One method of chemical treatment with an amine is by heat-treating the polyester in a solution of the amine and an organic solvent, or in a solution of the amine and a mixed solvent consisting of an organic solvent and water.

A separating agent consisting of a polyester chemically bonded to a core-shell particle can be obtained by causing a reaction between the chemically treated polyester and the surface treated core-shell particle in vacuum or air.

3. Protein

A protein may be used as the ligand of the separating agent of the present invention. Examples of proteins that can be used in the present invention include substances that have a molecular weight of 3 to 300 kDa or preferably 30 to 150 kDa, and that have affinity for the object of separation, which may be an antibody or other protein for example.

Of these, Protein A, Protein G, Protein L, albumin and functional variants of these are desirable as ligands because of their high selectivity when used for separating antibody proteins.

In cases when separation of an antibody is the main purpose, the ligand is preferably a substance capable of specifically combining with part of immunoglobulin.

The term "functional mutant" means a protein which has at least one modification in the natural amino acid sequence and which still retains at least one of the functions that accompany the natural sequence. Natural sequences include amino acid sequences that spontaneously arise. Examples of changes in amino acids include replacement of one or more amino acids with different amino acids, elimination of one or more amino acids and/or addition of one or more amino acids, or combinations of any of these. Examples thereof further include combinations of addition, elimination, and replacement to be conducted on a natural sequence. The functional mutants may contain a fragment or domain of a protein. The amino acid sequence of each functional mutant may be identical with the natural amino acid sequence to a degree of at least 70%, at least 75%, at least 80%, at least 85%, at least 90%, at least 95%, or at least 98%, and the functional mutant still retains at least one of the functions which accompany the natural sequence.

Examples of albumin include egg albumin and human serum albumin (molecular weight about 66 kDa).

Other examples of proteins that can be used in the present invention include the cellobiohydrolases (CBH) shown below, which are known as cellobiohydrolase I and II. Cellobiohydrolase I (CBH I) and cellobiohydrolase II (CBH II) are known as principal enzymes that constitute the majority of cellulases (80% or more for both, with the remainder made up of small quantities of endoglucanase, beta-glucosidase and the like). One method of manufacturing these is by using gene recombination techniques to cause large-volume expression of the target cellobiohydrolase in host cells.

An $\alpha_1$-acidic glycoprotein may be used as a protein in the present invention. An $\alpha_1$-acidic glycoprotein may be derived from humans, cows, rabbits or other mammals, or from chickens, swans, turkeys or other birds. Of these, specific examples of desirable $\alpha_1$-acidic glycoproteins include human $\alpha_1$-acidic glycoprotein (hereunder sometimes called "h-AGP") and chicken AGP (hereunder sometimes called "c-AGP").

A commercial product (from Sigma-Aldrich for example) may be used for the human $\alpha_1$-acidic glycoprotein (h-AGP), and may be purified as necessary by high-performance liquid chromatography.

Chicken $\alpha_1$-acidic glycoprotein (c-AGP) that for use in the present invention can be obtained by subjecting raw chicken ovomucoid to liquid chromatography using a cation exchange carrier (such as SP-Sepharose), by separating the chicken $\alpha_1$-acidic glycoprotein (c-AGP) from the ovomucoid by stepwise elution using an ammonium acetate buffer (pH 4.6).

A fraction containing c-AGP can also be further sampled out, and purified with an ion exchange chromatography carrier such as SP-Sepharose.

The aforementioned human $\alpha_1$-acidic glycoprotein is a glycoprotein consisting of 183 amino acid residues and 5 sugar chains, with a molecular weight of about 41000 to 43000. The chicken $\alpha_1$-acidic glycoprotein has the same amino acid residues and sugar chains as the human $\alpha_1$-acidic glycoprotein, but its molecular weight is about 30000.

The fixed amount of the protein on the core-shell particle is preferably 1.0 to 25 parts by weight per 100 parts by weight of the core-shell particle.

Normally a method such as the following is used to fix the protein by chemical bonding on the core-shell particle, but this is not a limitation.

The method used for immobilization may be a method in which a reactive functional group is first bonded to the core-shell particle, and this reactive functional group is then reacted directly with a functional group of the protein, or a method of bonding via a low-molecular-weight or high molecular-weight substance having in the molecule both one or more functional groups capable of reacting with a functional group of the protein and one or more functional groups capable of reacting with a functional group bonded to the core-shell particle (such compounds are generally called "spacers" below).

As an example of the former method, when immobilizing a ligand such as Protein A that has an amino group, a functional group that forms a covalent bond with an epoxy group or other amino group is provided on the core-shell particle by surface treatment with a silane coupling agent or the like containing epoxy groups, and is reacted directly with the Protein A to immobilize the protein.

Examples of the latter method include a method using an amino acid (aminecarboxylic acid) as a spacer, an amino group site of which is reacted with an epoxy group introduced into the core-shell particle, after which the spacer is reacted with an amino group of the Protein A by means of a carboxyl group of another terminal; and a method using a diamine or diol and a diglycidyl compound such as (poly)ethylene glycol diglycidyl ether sequentially as spacers, in which an epoxy group introduced into the core-shell particle is bonded to one terminal of the diamine or diol, and one epoxy group of the diglycidyl compound is bonded to the other terminal, while the epoxy group of the remaining terminal is bonded to the Protein A.

Examples of the diamine used as one component of the spacer in the above method include tetramethylene diamine, hexamethylene diamine and other aliphatic diamines, while examples of the diol include propylene glycol, butane diol, diethylene glycol, triethylene glycol and other aliphatic diols and polyethylene glycols.

Considering reactivity with the ligand and the issue of steric hindrance with the core-shell particle during immobilization, the spacer preferably has a straight-chain structure. Using a spacer with a branched structure, steric hindrance is greater, which can inhibit the formation of affinity bonds with the protein ligand and the antibody that is the object of separation, detracting from separation performance.

The reactive group introduced into the core-shell particle may be a 3-aminopropyl group introduced using 3-aminopropyl triethoxysilane, and in this case the core-shell particle is first reacted with a carbonate disuccinate diimide (N,N'-disuccinimidyl carbonate: DSC), and this is then reacted with an amino group of an amino acid residue of the protein.

4. Nucleic Acid

A nucleic acid can be used as the ligand of the separating agent of the invention. Such nucleic acid is not particularly limited, and examples thereof include DNA, RNA, oligonucleotides, and modified oligonucleotides. Derivatives of DNA and RNA can also be used. Although the DNA and the RNA may be of the natural or artificial type, it is preferred to use the artificial type which is structurally stable, when the stability of the separating agent is taken into account. In the artificial type, a sequence which does not exist in the natural type can be formed.

The number of bases of the artificial-type nucleic acids is preferably about 50 to 200 thereamong. From the standpoint of enabling efficient synthesis, it is preferred to use an artificial nucleic acid having about 100 bases. It is preferable that the artificial-type nucleic acids should have no adjoining thymine bases from the standpoint of preventing dimerization of thymine.

Furthermore, the nucleic acids may have been derivatized with a protective group in view of the durability of the separating agent. Specifically, the hydroxy group(s) at the 5'-position and/or the 3'-position can be derivatized using a phosphoric ester group, acyl group, alkoxycarbonyl group, benzyl group, substituted benzyl group, allyl group, etc.

The fixed amount of the nucleic acid relative to the core-shell particle is preferably 1.0 to 25 parts by weight per 100 parts by weight of the core-shell particle. If the fixed amount of the nucleic acid is less than 1.0 parts by weight per 100 parts by weight of the core-shell particle, the nucleic acid will not be stable in the separating agent, and adequate separation performance will not be obtained. On the other hand, if the fixed amount of the nucleic acid exceeds 25 parts by weight per 100 parts by weight of the core-shell particle, it may not be possible to fix the nucleic acid on the core-shell particle, resulting in in the production of free nucleic acids and adversely affecting the separation performance.

One method of fixing the nucleic acid on the core-shell particle is a method of bonding via chitosan and the amino groups of chitosan, as described in Japanese Patent Application Publication No. 2010-259405. In this method, the core-shell particle is first modified as follows with an aminosilane such as 3-aminopropyl triethoxysilane, glutaraldehyde, chitosan, glutaraldehyde and avidin successively.

The core-shell particle is subjected to a condensation reaction with 3-aminopropyl triethoxysilane, and then heat treated.

The 3-aminopropyl triethoxysilane-treated core-shell particle is dipped in a glutaraldehyde solution, and then washed and air dried.

The glutaraldehyde-treated core-shell particle is dipped in a chitosan solution, and then washed with ultrapure water. This serves to covalently bond the amino groups of the chitosan to the aldehyde groups of the glutaraldehyde, producing multiple amino groups on the surface of the core-shell particle and increasing the surface area available for bonding the nucleic acid.

Next, the core-shell particle with the introduced chitosan is dipped in a glutaraldehyde solution, and then washed and air dried.

An avidin solution is dripped onto the resulting core-shell particle, which is then left standing to bond the amino groups of the avidin with the aldehyde groups and fix the avidin to the core-shell particle via the chitosan.

A biotin-labeled nucleic acid solution is then dripped onto the core-shell particle with the avidin fixed thereon, and reacted to produce a core-shell particle with the nucleic acid immobilized thereon via the chitosan.

5. Optically-Active Compound with Molecular Weight of 50 to 1000

An optically-active organic compound with a molecular weight of 50 to 1000 can be used as the ligand of the separating agent of the present invention. This organic compound is not particular limited as long as it has an asymmetric center and a molecular weight of 50 to 1000, and is capable of bonding to the core-shell particle by chemical bonding.

5-(1) Compound Having Binaphthyl Structure and Crown Ether-Like Cyclic Structure A compound having a binaphthyl structure and a crown ether-like cyclic structure in the molecule is described for example in Japanese Patent Application Publication No. 2003-327675.

Another desirable example is the compound represented by Formula (III) below for example.

[C3]

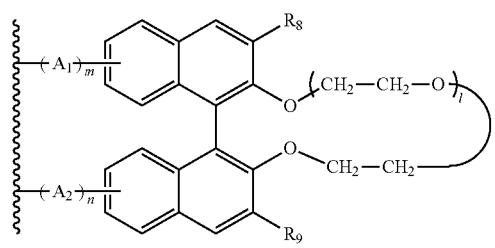

(III)

In Formula (III), each of $R_8$ and $R_9$ represents hydrogen, an optionally substituted phenyl group, an optionally substituted naphthyl group, an optionally substituted $C_{1-8}$ alkyl group in which any discontinuous methylene group may be oxygen, or a trialkylsilyl group in which each alkyl group has 1 or 2 carbon atoms. An optional substituent of a phenyl group or the like in $R_8$ and $R_9$ is a group that does not interact with an oxygen atom of the crown ether-like cyclic structure, and examples of such substituents include methyl and chloro groups. $R_8$ and $R_9$ are preferably phenyl groups from the standpoint of improving separation performance.

In Formula (III), each of $A_1$ and $A_2$ represents a group substituted for a hydrogen of the binaphthyl ring and bonded to the surface of the carrier. The size of $A_1$ and $A_2$ is not particularly limited, but for ease of synthesis and to improve separation performance, the molecular weight of each is preferably 100 to 600. $A_1$ and $A_2$ may be composed of various groups such as $C_{1-30}$ alkylene groups, $C_{6-30}$ arylene groups, ether groups, carbonyl groups, imino groups, amido groups and the like.

From the standpoint of ease of synthesis of the binaphthyl compound, it is desirable that $A_1$ and $A_2$ each contain structures represented by Formula (IV) below substituted for hydrogen atoms of the binaphthyl in Formula (III).

[C4]

(IV)

In Formula (IV), o represents an integer from 1 to 30. For ease of synthesis and improving separation performance, o is preferably between 4 and 10.

In Formula (III), l is an integer from 4 to 6. Such an l is desirable for purposes of including ammonium ions, and 4 is especially desirable.

In Formula (III), each of m and n is an integer from 0 to 5, with m+n being 1 to 10. For ease of synthesis of the binaphthyl compound, is desirable that m and n both be 1 or greater, and more desirable that one of m and n be 1 while the other is 0. If m or n is 0, this means that there is no bonding with the carrier.

The method of chemically bonding the compound represented by Formula (III) to the core-shell particle may involve the steps A to D shown below.

The chromatography separating agent of the present invention may be manufactured by a method comprising a step A of introducing a carrier linking group into the binaphthyl ring of the binaphthyl derivative A represented by Formula (III) below to obtain a binaphthyl derivate B, a step B of hydrolyzing the methoxy groups of the 2,2' sites of the binaphthyl derivative B to convert the methoxy groups to hydroxyl groups and obtain a binaphthyl derivative C, a step C of crosslinking each of these hydroxyl groups of the binaphthyl derivative C with a polyethylene glycol derivative to obtain a binaphthyl derivative D having a crown ether-like cyclic structure, and a step D of bonding the binaphthyl derivative D by chemical bonding to the surface of the core-shell particle via the carrier linking group of the binaphthyl derivative D.

[C5]

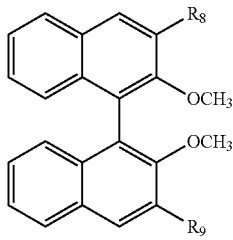

(V)

In Formula (V), $R_8$ and $R_9$ are the same as the $R_8$ and $R_9$ of the Formula (III). The binaphthyl derivative A can be obtained as a commercial product. Examples of such commercial products include 2,2'-dimethoxy-1,1'-binaphthyl and 3,3'-dibromo-2,2'-dimethoxy-1,1'-binaphthyl (both products of Tokyo Chemical Industry Co., Ltd). Using such a commercial product is desirable for facilitating the synthesis of the binaphthyl compound.

The binaphthyl derivative A may also be obtained by synthesis. The binaphthyl derivative A may be obtained by synthesis from 3,3'-dibromo-2,2'-dimethoxy-1,1'-binaphthyl. This method of the invention is desirable because a greater diversity of $R_8$ and $R_9$ in the binaphthyl compound is obtained by including a further step of substituting $R_8$ and $R_9$ for each of the bromo groups of 3,3'-dibromo-2,2'-dimethoxy-1,1'-binaphthyl to obtain the binaphthyl derivative A.

In the step A, the carrier linking group may be a group that bonds to a functional group on the surface of the core-shell particle, or a group that bonds directly to the surface of the core-shell particle. There may be one kind of two or more kinds of carrier linking groups. One carrier linking group is sufficient, but there may also be two or more. When there are two or more carrier linking groups, the carrier linking groups may bond to only one of the two naphthyl rings of the binaphthyl, or one may bond to each. From the standpoint of ease of bonding between the binaphthyl derivative D and the core-shell particle, the carrier linking group is preferably a group that bonds to a functional group produced by surface treatment of the core-shell particle.

A desirable example of such a step A is a step of reacting the binaphthyl derivative A with a $C_{4-33}$ aliphatic dicarboxylic monomethyl ester monochloride in the presence of iron chloride to obtain the binaphthyl derivative B.

The step B can be accomplished by a reaction under mild conditions because the 2,2' site of the binaphthyl is highly reactive even in the binaphthyl derivative B. An example of such reaction conditions is a dealkylation reaction with boron tribromide at a temperature between ice-cooled and room temperature. Performing the step B under such conditions is desirable from the standpoint of controlling the effect on other structures of the binaphthyl derivative B, and obtaining the binaphthyl derivative C with a greater yield.

The step C may be performed under conditions that serve to crosslink polyoxyethylene to the hydroxyl groups of the 2,2' site of binaphthyl derivative C. Such crosslinking can be accomplished by hydrolysis, and for example can be accomplished by reacting polyoxyethylene glycol ditosylate with 5 to 7 repeating oxyethylene groups under alkaline conditions.

The step D may be accomplished appropriately within the range of known techniques according to the carrier linking group and the type of surface treatment of the core-shell particle. For example, when using a surface treated core-shell particle, the step D may be accomplished by chemically bonding the carrier linking groups of the binaphthyl derivative D with functional groups produced by surface treatment of the core-shell particle.

A silane coupling agent may be used as the surface treatment agent for the core-shell particle. Examples of such silane coupling agents include 3-aminopropyl triethoxysilane and 3-(2-aminoethylaminopropyl)trimethoxysilane.

The fixed amount of the compound represented by the formula (III) on the core-shell particle is preferably 1.0 to 25 parts by weight per 100 parts by weight of the core-shell particle.

5-(2) N-acylated Amino Acid, N-carbamoyl Amino Acid, N-carbamoyl-α-aromatic Amino Acid In the separating agent of the present invention, a N-acylated amino acid, N-carbamoyl amino acid or N-carbamoyl-α-aromatic amino acid (hereunder called an amino acid of the present invention) may be fixed as a ligand by chemical bonding on the core-shell particle to obtain a separating agent for optical isomers.

Examples of N-acylated amino acids include N-pivaloyl-L-valine, N-3,5-dinitrobenzoyl-D-phenylglycine and the like. Examples of N-carbamoyl amino acids include N-carbamoyl-leucine, N-carbamoyl-valine and the like. Examples of N-carbamoyl-α-aromatic alkylamines include N-carbamoyl-α-(nonaphthyl)ethylamine and the like.

This amino acid of the present invention functions as a chiral site in the separating agent of the present invention.

One method of chemically bonding the amino acid of the present invention to the core-shell particle is as follows. The specific operations are described in Japanese Patent Application Publication No. H5-4045.

First, the core-shell particle is surface treated with a silane coupling agent having amino groups, such as 3-aminopropyl triethoxysilane, to introduce aminopropyl groups into the core-shell particle. The introduced aminopropyl groups function as anchor sites. Examples of silane coupling agents other than 3-aminopropyl triethoxysilane include 6-aminohexyl alkoxysilane, 6-aminohexyl halogenosilanes, 3-aminopropyl trihalogenosilanes and the like. A preferred example of a 3-aminopropyl halogenosilane is 3-aminopropyl trichlorosilane.

—NH—$(CH_2)_n$—CO— (in which n is 5 or more, or preferably 5 to 10) is further introduced as a sub-anchor site between the chiral site and the anchor site. If n is less than 5 the separating ability of the packing material is diminished. If n exceeds 10, on the other hand, there is an increase in interactions between chiral sites and interactions between hydrophobic groups that are unnecessary for molecular discrimination, detracting from the separating ability.

An example of a compound used to form this sub-anchor site is aminoalkanoic acid. An operation is performed to protect this aminoalkanoic acid with a methyl ester or other ester.

Next, the amino acid of the present invention is reacted with a carboxylic acid activation reagent such as N-hydroxysuccinic acid imide to perform esterification. This is reacted with the aminoalkanoic acid methyl ester obtained by esterification above to bond the chiral site to the sub-anchor site. The carboxyl group of the sub-anchor site can then be reacted with the amino group of the anchor site to fix the amino acid of the present invention by chemical bonding on the core-shell particle.

The fixed amount of the amino acid of the present invention relative on the core-shell particle is preferably 1.0 to 25 parts by weight per 100 parts by weight of the core-shell particle.

When an optically active ligand is used, the separating agent of the present invention may be used as a separating agent for optical isomers, while when an optically inactive ligand is used, it can be used as a separating agent for affinity chromatography. These separating agents can also be used as packing materials for gas chromatography or electrophoresis, and particularly for the capillary columns of capillary electrochromatography (CEC), CZE (capillary zone electrophoresis) and MEKC (micellar electrokinetic chromatography).

EXAMPLES

The present invention is explained in detail by means of examples, but the present invention is not limited to these examples. The number of theoretical stages (N), retention coefficient (k') and separation coefficient (α) in the examples below are defined by the following formulae.

Number of Theoretical Stages $N = 16 \times [(\text{retention time})/(\text{peak width})]^2$ Retention Coefficient $k' = [(\text{retention time of enantiomer}) - (\text{dead time})]/(\text{dead time})$ Separation Coefficient $\alpha = (\text{retention time of strongly retained enantiomer})/(\text{retention time of weakly retained enantiomer})$ The dead time here is the elution time of tri-tert-butylbenzene.

Example 1

Method for Preparing Packing Material Comprising 2 wt % Cellulose-Tris(3,5-Dichlorophenylcarbamate) Fixed by Photocrosslinking Immobilization, and Packing Column Preparation Method (1) Synthesis of cellulose tris(3,5-dichlorophenylcarbamate) (1)

Commercial 3,5-dichlorophenylisocyanate and cellulose were reacted in a pyridine solvent, to obtain a white solid (1). Non-patent Document 2 was consulted for the reaction conditions.

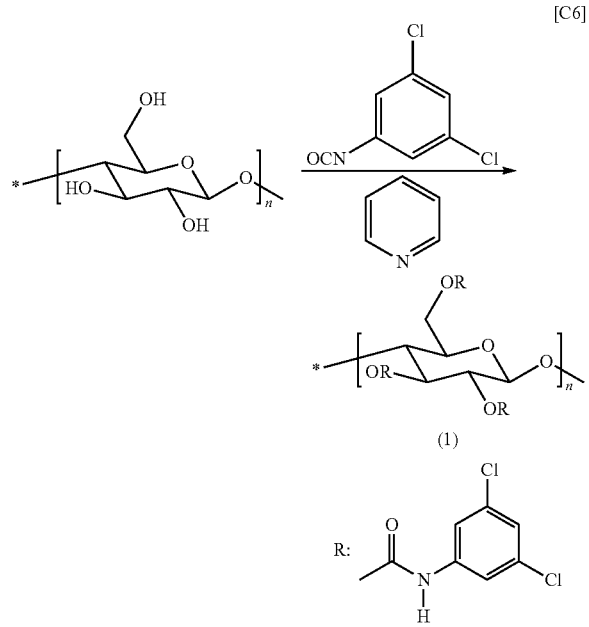

[C6]

(2) Preparation of Packing Material Comprising 2 wt % cellulose tris(3,5-dichlorophenylcarbamate) (1) Fixed by Physical Adsorption.

0.081 g of the cellulose derivative (1) obtained in (1) was dissolved in 30 mL of tetrahydrofuran. 3.9 g of core-shell silica gel (packing material removed from ChromaNik Technologies di. 4.5 cm×L 15 cm special column (particle size 2.6 μm, pore diameter 9 nm, C4 core-shell), heated for 1 hour to 600° C. in electric furnace, held for 5 hours to cool, dispersed in 4 N hydrochloric acid, agitated overnight, washed in pure water and dried, particle size: 2.6 μm, pore diameter: 9 nm (catalog values), core diameter: 1.6 μm, core material: glass, shell thickness: 0.5 μm, shell material: silica gel (polyalkoxysiloxane hydrolysate)) was added to this solution and agitated by shaking for several minutes, and the solvent was distilled off under reduced pressure to prepare a packing material comprising 2 wt % of fixed cellulose tris(3,5-dichloro phenylcarbamate) (1).

(3) Preparation of Packing Material Comprising 2 wt % of cellulose tris(3,5-dichlorophenylcarbamate) (1) Fixed by Immobilization 2.76 g of packing material with 2 wt % of fixed cellulose tris(3,5-dichlorophenylcarbamate) (1) was suspended in 500 mL of acetonitrile/water=60/40 (vol/vol), and agitated. The suspension was irradiated for 10 minutes with an immersive mercury lamp (Philips, HPK-125 watt, quartz casing). The precipitate was filtered out, washed with tetrahydrofuran, and dried.

(4) Preparation of Packing Column Using Packing Material Comprising 2 wt % Cellulose tris(3,5-dichlorophenylcarbamate) (1) Fixed by Immobilization The supporting packing material prepared in (3) was pressed and packed by the slurry packing method in a di. 0.21 cm×L 15 cm stainless steel column to prepare a column.

Applied Example 1

Using the optical isomer separation column prepared in Example 1, the column performance (N value) and separation coefficient of the optical isomer separation column were evaluated by liquid chromatography using a compound having the following structure (trans-stylbene oxide).

[C7]

As a comparative example, the column performance (k' value, α value, N value) of an optical isomer separation column using a packing material comprising 2.0 wt % of cellulose tris(3,5-dichlorophenylcarbamate) (1) fixed on completely porous silica gel (particle size 5 μm, pore diameter 12 nm) by the method described in Example 1 were also given. For the evaluation conditions, n-hexane/2-propanol=90/10 was used as the mobile phase, with a flow rate of 0.15 mL/min and the temperature set at 25° C. in both Example 1 and the comparative example.

TABLE 1

Column performance (N value) in Example 1 and comparative example

| Racemate | Separating agent | |
| --- | --- | --- |
| | Example 1: 2.0 wt % fixed on core-shell | Comparative Example: 2.0 wt % fixed on completely porous gel |
| Trans-stylbene oxide | K1' = 0.157, k2' = 0.216, α = 1.413 | k1' = 0.184, k2' = 0.207, α = 1.123 |

Example 2

Method for Preparing Packing Material Comprising 10 wt % Cellulose-Tris(3,5-Dichlorophenylcarbamate) Fixed by Photocrosslinking Immobilization, and Packing Column Preparation Method (1) Preparation of Packing Material Comprising 10 wt % Cellulose tris(3,5-dichlorophenylcarbamate) (1) Fixed by Physical Adsorption 0.4 g of the cellulose derivative (1) obtained in (1) of Example 1 was dissolved in 4 mL of tetrahydrofuran. This solution was coated uniformly on 3.5 g of core-shell silica gel (Advanced Materials Technology (AMT), particle size: 2.7 μm, pore diameter: 16 nm (catalog value), core diameter: 1.7 μm, core material: glass, shell thickness: 0.5 μm, shell material: silica gel (polyalkoxysiloxane hydrolysate), heated for 1 hour to 600° C. in an electric furnace, then held for 5 hours to cool, dispersed in 4 N hydrochloric acid, agitated overnight, washed with pure water and dried), and the tetrahydrofuran was distilled off under reduced pressure to prepare a packing material comprising 10 wt % of fixed cellulose tris(3,5-dichlorophenylcarbamate) (1).

(2) Preparation of Packing Material Comprising 10 wt % of Cellulose Tris(3,5-dichlorophenylcarbamate) (1) Fixed by Immobilization 3.6 g of packing material with 10 wt % of fixed cellulose tris(3,5-dichlorophenylcarbamate) (1) was suspended in 500 mL of acetonitrile/water=60/40 (vol/vol), and agitated. The suspension was irradiated for 10 minutes with an immersive mercury lamp (Philips, HPK-125 watt, quartz casing). The precipitate was filtered out, washed with tetrahydrofuran, and dried. The supported amount was 9.5% according to the results of element analysis.

(3) Preparation of Packing Column Using Packing Material Comprising 10 wt % Cellulose tris(3,5-dichlorophenylcarbamate) (1) Fixed by Immobilization The supporting packing material prepared in (2) was pressed and packed by the slurry packing method in a di. 0.21 cm×L 15 cm stainless steel column to prepare a column.

Example 3

Method for Preparing Packing Material Comprising Immobilized Cellulose-tris(3,5-dichlorophenylcarbamate) (2) having Alkoxysily Groups, and Packing Column Preparation Method (1) Synthesis of Cellulose tris(3,5-dichlorophenylcarbamate) (2) having Alkoxysilyl Groups Cellulose was reacted with 3,5-dichlorophenylisocyanate and 3,5-(triethoxysilyl)propyl isocyanate to obtain cellulose tris(3,5-dichlorophenylcarbamate) (2) having alkoxysilyl groups. The methods described in Example 2 of Patent Document 1 were consulted for the reaction conditions. According to the results of 1H-NMR, the introduction rates of 3,5-dichlorophenylisocyanate and alkoxysilyl groups (ethoxysilyl groups) were 97.4% and 2.6%, respectively.

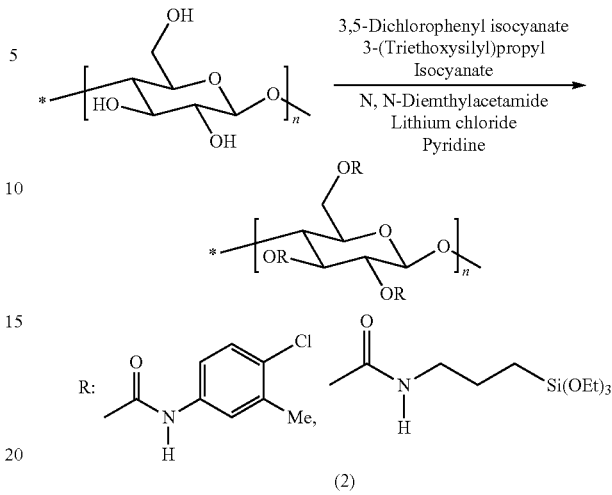

(2) Preparation of Packing Material Comprising 10 wt % of Cellulose tris(3,5-dichlorophenylcarbamate) (2) having Alkoxysilyl Groups, Fixed by Physical Adsorption 0.4 g of the cellulose derivative (2) having alkoxysilyl groups obtained in (1) was dissolved in 3.2 mL of tetrahydrofuran. This solution was coated uniformly on 3.6 g of core-shell silica gel that had been surface treated with 3-aminopropyl triethoxysilane (manufactured by known methods from Advanced Materials Technology (AMT) gel, particle size: 2.7 μm, pore diameter: 16 nm (catalog value), core diameter: 1.7 μm, core material: glass, shell thickness: 0.5 μm, shell material: silica gel (polyalkoxysiloxane hydrolysate)), and the tetrahydrofuran was distilled off under reduced pressure to prepare a packing material comprising 10 wt % of fixed cellulose tris(3,5-dichlorophenylcarbamate) (2) having alkoxysilyl groups.

(3) Preparation of Packing Material Comprising Immobilized Cellulose tris(3,5-dichlorophenylcarbamate) (2) Having Alkoxysilyl Groups 3 g of the packing material obtained in (2) was dispersed in ethanol/water/chlorotrimethylsilane (27.5 mL/7 mL/0.45 mL), and reacted for 10 minutes while being boiled in a 110° C. oil bath to perform immobilization on the silica gel. This was washed in methanol and dried. The supported amount was 5.6% according to the results of element analysis.

(4) Preparation of Packing Column Using Packing Material with Immobilized Cellulose tris(3,5-dichlorophenylcarbamate) (2) having Alkoxysilyl Groups The supporting packing material prepared in (3) was pressed and packed by the slurry packing method in a di. 0.21 cm×L 15 cm stainless steel column to prepare a column.

Example 4

Method for Preparing Packing Material Comprising Chemical Bonded Cellulose Tris(3,5-Dichlorophenylcarbamate) (1), and Packing Column Preparation Method (1) Preparation of Packing Material Comprising Chemically Bonded Cellulose tris(3,5-dichlorophenylcarbamate) (1)

5 g of a substance consisting of cellulose chemically bonded to core-shell silica gel surface treated with aminopropyl triethoxysilane (manufactured by known methods from Advanced Materials Technology (AMT), particle size: 2.7

μm, pore diameter: 16 nm (catalog value), core diameter: 1.7 μm, core material: glass, shell thickness: 0.5 μm, shell material: silica gel (polyalkoxysiloxane hydrolysate) that was heated for 1 hour to 600° in an electric furnace, held for 5 hours to cool, dispersed in 4 N hydrochloric acid, agitated overnight, washed in pure water and dried) was synthesized with reference to the methods described in Example 1 of Patent Document 11. However, in this case a substance comprising cellulose chemically bonded to core-shell silica gel was obtained using 5 times the input amount of cellulose described in the patent document. 4 g of the resulting cellulose-bonded core-shell silica gel was suspended in a mixed solvent consisting of N,N-dimethylacetamide and pyridine, 3.1 g of 3,5-dichlorophenyl isocyanate was added, and a reaction was performed for 48 hours at 80° C. The suspension was filtered, washed with methanol, and dried. The supported amount was 0.9% according to the results of element analysis.

(2) Preparation of Packing Column Using Packing Material Comprising Chemically Bonded Cellulose tris(3,5-dichlorophenylcarbamate) (1)

The supporting packing material prepared in (1) was pressed and packed by the slurry packing method in a di. 0.21 cm×L 15 cm stainless steel column to prepare a column.

Example 5

Method of Preparing Packing Material Comprising Chemically Bonded Polybutylene Terephthalate, and Packing Column Preparation Method (1) Preparation of Packing Material Comprising 10 wt % of Polybutylene Terephthalate (3) Fixed by Physical Adsorption 0.4 g of polybutylene terephthalate (Duranex 300FP) (3) was dissolved in 4 mL of 1,1,1,3,3,3-hexafluoroisopropanol (HFIPA). This solution was coated uniformly on 3.6 g of core-shell silica gel that had been surface treated with 3-aminopropyl triethoxysilane (manufactured by known methods from Advanced Materials Technology (AMT) gel, particle size: 2.7 μm, pore diameter: 16 nm (catalog value), core diameter: 1.7 μm, core material: glass, shell thickness: 0.5 μm, shell material: silica gel (polyalkoxysiloxane hydrolysate)), and the HFIPA was distilled off under reduced pressure to prepare a packing material comprising 10 wt % of fixed polybutylene terephthalate (3).

(2) Preparation of Packing Material Comprising Chemically Bonded Polybutylene Terephthalate (3)

2.5 g of the packing material obtained in (1) was reacted for 3 hours in an oven at 200° C., to perform immobilization on the silica gel. This was washed with HFIPA and dried. The supported amount was 7.7% according to the results of element analysis.

(3) Preparation of Packing Column Using Packing Material Comprising Chemically Bonded Polybutylene Terephthalate (3)

The supporting packing material prepared in (2) was pressed and packed by the slurry packing method in a di. 0.21 cm×L 15 cm stainless steel column to prepare a column.

Example 6

Method for Manufacturing Packing Material with Chemically Bonded Polyethylene Terephthalate, and Packing Column Preparation Method (1) Preparation of Packing Material Comprising 10 wt % of Polyethylene Terephthalate (Teijin Limited, TR8550FF) (4) Fixed by Physical Adsorption 0.4 g of polyethylene terephthalate (4) was dissolved in a mixed solvent consisting of 2.0 mL of 1,1,1,3,3,3-hexafluoroisopropanol (HFIPA) and 2.0 mL of dichloromethane. This solution was coated uniformly on 3.6 g of core-shell silica gel that had been surface treated with 3-aminopropyl triethoxysilane (manufactured by known methods from Advanced Materials Technology (AMT) gel, particle size: 2.7 μm, pore diameter: 16 nm (catalog value), core diameter: 1.7 μm, core material: glass, shell thickness: 0.5 μm, shell material: silica gel (polyalkoxysiloxane hydrolysate)), and the HFIPA and dichloromethane were distilled off under reduced pressure to prepare a packing material comprising 10 wt % of fixed polyethylene terephthalate (4).

(2) Preparation of Packing Material Comprising Chemically Bonded Polyethylene Terephthalate (4)

2.5 g of the packing material obtained in (1) was reacted for 3 hours in an oven at 200° C., to perform immobilization on the silica gel. This was washed with HFIPA, and dried. The results of element analysis showed a supported amount of 7.1%.

(3) Preparation of Packing Column Using Packing Material Comprising Chemically Bonded Polyethylene Terephthalate (4)

The supporting packing material prepared in (2) was pressed and packed by the slurry packing method in a di. 0.21 cm×L 15 cm stainless steel column to prepare a column.

Example 7

Method of Manufacturing Packing Material Comprising Chemically Bonded (S)-[1,2-[6-(5-carboxypentanoyl)]-(3-phenylnaphtho)]-[1',2'-(3'-phenylnaphtho)]-1,6,9,12,15,18-hexaoxa-cycloeicosa-2,4-diene, and Packing Column Preparation Method (1) Synthesis of (S)-[1,2-[6-(5-carboxypentanoyl)]-(3-phenylnaphtho)]-[1',2'-(3'-phenylnaphtho)]-1,6,9,12,15,18-hexaoxa-cycloeicosa-2,4-diene (5)

The chiral crown ether (5) was synthesized by the methods described in paragraphs [0057] to [0064] of the Examples of Patent Document 12.

[C9]

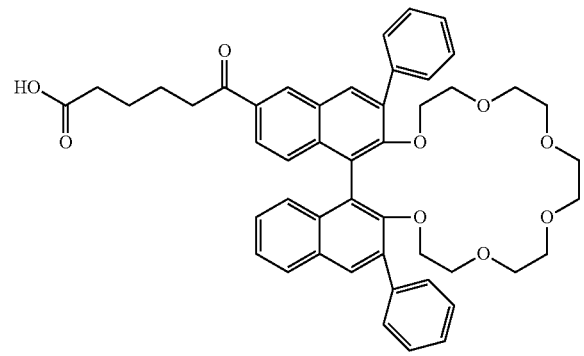

(5)

(2) Preparation of Packing Material Comprising Chemically Bonded (S)-[1,2-[6-(5-carboxypentanoyl)]-(3-phenylnaphtho)]-[1',2'-(3'-phenylnaphtho)]-1,6,9,12,15,18-hexaoxa-cycloeicosa-2,4-diene (5)

0.21 g of the chiral crown ether (5), 0.16 g of O-(7-azabenzotriazol-1-yl)-N,N,N',N'-tetramethyluronium hexafluorophosphate and 42 μL of N-methyl morpholine were dissolved in 15 mL of N,N-dimethylformamide and added to 1.97 g of core-shell silica gel that had been surface treated with 3-aminopropyl triethoxysilane (manufactured by known methods from Advanced Materials Technology (AMT), particle size:

2.7 µm, pore diameter: r 16 nm (catalog value), core diameter: 1.7 µm, core material: glass, shell thickness: 0.5 µm, shell material: silica gel (polyalkoxysiloxane hydrolysate)), and reacted for 4 hours at room temperature. This was washed with a dilute hydrochloric acid/methanol solution and N,N-dimethylformamide. The resulting packing material was dispersed in 15 mL of N,N-dimethylformamide, 3.2 g of pyridine and 1.87 g of anhydrous acetic acid were added, and the mixture was reacted for 3 hours at room temperature. This was washed with N,N-dimethylformamide and methanol, and dried. The results of element analysis showed a carrying arte of 7.1%.

(3) Preparation of Packing Column Using Packing Material Comprising Chemically Bonded (S)-[1,2-[6-(5-carboxypentanoyl)]-(3-phenylnaphtho)]-[1',2'-(3'-phenylnaphtho)]-1,6,9,12,15,18-hexaoxa-cycloeicosa-2,4-diene (5)

The supporting packing material prepared in (2) was pressed and packed by the slurry packing method in a di. 0.21 cm×L 15 cm stainless steel column to prepare a column.

Example 8

Method of Manufacturing Packing Material Comprising Chemically Bonded Human Serum Albumin (HAS), and Packing Column Preparation Method (1) Preparation of Packing Material Comprising Chemically Bonded Human Serum Albumin (HAS)

1.0 g of core-shell silica gel that had been surface treated with 3-aminopropyl triethoxysilane (manufactured by known methods from Advanced Materials Technology (AMT), particle size: 2.7 µm, pore diameter: 16 nm (catalog value), core diameter: 1.7 µm, core material: glass, shell thickness: 0.5 µm, shell material: silica gel (polyalkoxysiloxane hydrolysate)) and 1.0 g of N,N'-disuccinimidyl carbonate (DSC) were suspended in a solution dissolved in 50 mL acetonitrile, and agitated for 17 hours at 30° C. This solution was filtered, and washed successively with acetonitrile, water, methanol and acetonitrile. The filter residue was dried to obtain N-hydroxysuccinimidyl (NHS)-activated silica gel.

0.5 g of the resulting NHS-activated silica gel was placed in 20 mL of 20 mM phosphate buffer (pH 6.8), a solution of 30 mg of HSA (Sigma-Aldrich, purity 99%) dissolved in 20 mL of 20 mM phosphate buffer (pH 6.8) was added over the course of 30 minutes with the pH maintained at 6.8, and the mixture was agitated for 17 hours at 4° C. This solution was filtered, and washed with 100 mL of water. A solution of 1.4 g of glucosamine hydrochloride dissolved in 20 mL of 20 mM phosphate buffer (pH 6.8) was added to the filter residue, and agitated for 1 hour at room temperature. This solution was filtered, and washed successively with water and 10% ethanol water to obtain a packing material comprising immobilized HAS. An assay of HAS in the reaction filtrate by the Bradford method showed a supported amount of 3.5%.

(2) Preparation of Packing Column Using Packing Material Comprising Chemically Bonded Human Serum Albumin (HAS)

The supporting packing material prepared in (1) was pressed and packed by the slurry packing method in a di. 0.21 cm×L 15 cm stainless steel column to prepare a column.

Applied Example 2

Using the optical isomer separation column prepared in Example 2, the column performance of the optical isomer separation column was evaluated by liquid chromatography using a trans-stylbene oxide with the structure shown above. The column performance (k' value, α value, N value) of an optical isomer separation column using a packing material (supported amount 8.6% according to element analysis) comprising 10 wt % of cellulose tris(3,5-dichlorophenylcarbamate) (1) fixed on completely porous silica gel (particle size 3 µm, pore diameter 30 nm) by the methods described in Example 2 was also given as Comparative Example 1. For the evaluation conditions, n-hexane/2-propanol=90/10 was used as the mobile phase with a flow rate of 0.15 mL/min and the temperature set at 25° C. in both Example 2 and Comparative Example 1.

Applied Example 3

Using the optical isomer separation column prepared in Example 3, the column performance of the optical isomer separation column was evaluated by liquid chromatography using a trans-stylbene oxide. The column performance (t value, α value) of an optical isomer separation column using a packing material (supported amount 4.6% according to element analysis) comprising cellulose tris(3,5-dichlorophenylcarbamate) (2) having alkoxysilyl groups immobilized on completely porous silica gel (particle size 3 µm, pore diameter 30 nm) by the methods described in Example 3 was also given as Comparative Example 2. For the evaluation conditions, n-hexane/2-propanol=90/10 was used as the mobile phase, with a flow rate of 0.15 mL/min and the temperature set at 25° C. in both Example 3 and Comparative Example 2.

TABLE 2

Column performance in Examples 2, 3, 4 and Comparative Examples 1, 2 (t value, α value)

| Separating agent | Racemate | |
|---|---|---|
| | Trans-stilbene oxide | 2-phenyl-cyclohexanone |
| Example 2: Core-shell, supported amount 9.5 wt % | t1 = 3.350<br>t2 = 4.130<br>α = 1.587 | t1 = 9.721<br>t2 = 11.674<br>α = 1.252 |
| Example 3: Core-shell, supported amount 5.6 wt % | t1 = 2.841<br>t2 = 3.290<br>α = 1.589 | |
| Example 4: Core-shell, supported amount 0.9 wt % | | t1 = 2.416<br>t2 = 2.480<br>α = 1.810 |
| Comparative Example 1: Completely porous, supported amount 8.6 wt % | t1 = 3.417<br>t2 = 3.775<br>α = 1.489 | t1 = 6.422<br>t2 = 7.272<br>α = 1.228 |
| Comparative Example 2: Completely porous, supported amount 4.6 wt % | t1 = 3.117<br>t2 = 3.329<br>α = 1.535 | |

Applied Example 4

Using the optical isomer separation columns prepared in Examples 5 and 6, column performance (t value, α1 value (o-terphenyl and m-terphenyl separation coefficient) and α2 value (m-terphenyl and p-terphenyl separation coefficient) was evaluated by liquid chromatography using the o-terphenyl, m-terphenyl and p-terphenyl shown below. The column performance (t value, α1 value, α2 value) of a column using a packing material (supported amount 8.5% according to element analysis) comprising polybutylene terephthalate (3) immobilized on completely porous silica gel (particle size 3 µm, pore diameter 12 nm) by the methods described in Example 5 was also given as Comparative Example 3. For the evaluation conditions, n-hexane/2-propanol=100/1 was used as the mobile phase, with a flow rate of 0.15 mL/min and the temperature set at 25° C. in Example 5, Example 6 and Comparative Example 3.

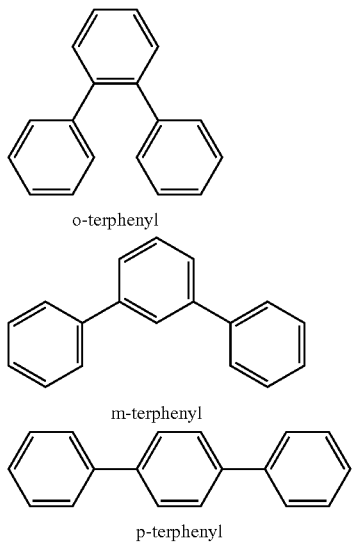

o-terphenyl m-terphenyl p-terphenyl

TABLE 3

Column performance of Examples 5 and 6 and Comparative Example 3 (t values)

| Compound | Separating agent | | |
|---|---|---|---|
| | Example 5: Core-shell, supported amount 7.7 wt % | Example 6: Core-shell, supported amount 7.1 wt % | Comparative Example 3: Completely porous, supported amount 8.5 wt % |
| o-terphenyl | t = 2.526 | t = 2.443 | t = 3.163 |
| m-terphenyl | t = 2.901 | t = 2.774 | t = 3.467 |
| p-terphenyl | t = 3.087 | t = 2.774 | t = 3.557 |
| Separation results: | 3-compound separation: | o-terphenyl separation only: | 3-compound separation: |
| α (1) | α1 = 1.977 | α1 = 2.100 | α1 = 1.578 |
| α (2) | α2 = 1.245 | α2 = 1.000 | α2 = 1.108 |

Applied Example 5

Using the optical isomer separation column prepared in Example 7, the column performance of the optical isomer separation column was evaluated by liquid chromatography using the following compounds (tyrosine, alanine, glutamic acid, α-amino-ε-caprolactam). The column performance (t value, α value) of an optical isomer separation column using a packing material (supported amount 9.1% according to element analysis) comprising (S)-[1,2-[6-(5-carboxypentanoyl)]-(3-phenylnaphtho)]-[1',2'-(3'-phenylnaphtho)]-1,6,9,12,15,18-hexaoxa-cycloeicosa-2,4-diene (5) chemically bonded to completely porous silica gel (particle size 3 µm, pore diameter 30 nm) by the methods described in Example 7 was also given as Comparative Example 4. For the evaluation conditions, aqueous perchloric acid solution (pH 1.5)/acetonitrile=80/20 was used as the mobile phase, with a flow rate of 0.10 mL/min and the temperature set at 25° C. in both Example 7 and Comparative Example 4.

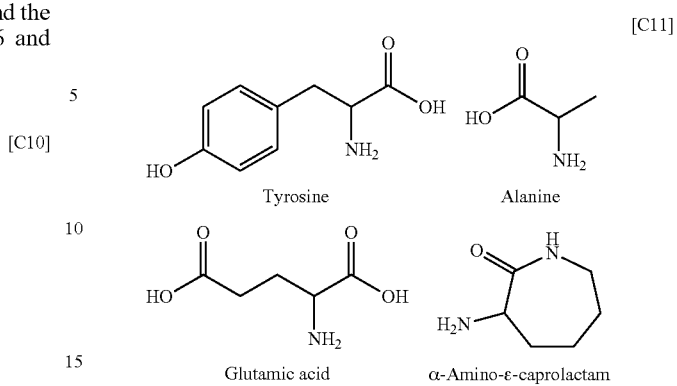

Tyrosine   Alanine

Glutamic acid   α-Amino-ε-caprolactam

TABLE 4

| Racemate | Separating agent | |
|---|---|---|
| | Example 7: Core-shell, supported amount 7.1 wt % | Comparative Example 4: Completely porous, supported amount 9.1 wt % |
| Tyrosine | t1 = 4.934 | t1 = 5.395 |
| | t2 = 8.784 | t2 = 7.842 |
| | α = 3.572 | α = 2.250 |
| Alanine | t1 = 3.753 | t1 = 4.512 |
| | t2 = 5.484 | t2 = 5.695 |
| | α = 6.478 | α = 2.100 |
| Glutamic acid | t1 = 3.699 | t1 = 4.468 |
| | t2 = 6.268 | t2 = 6.370 |
| | α = 10.805 | α = 2.845 |
| α-amino-ε-caprolactam | t1 = 3.797 | t1 = 4.497 |
| | t2 = 5.618 | t2 = 5.600 |
| | α = 6.058 | α = 2.041 |

Applied Example 6

Using the optical isomer separation column prepared in Example 8, the column performance of the optical isomer separation column was evaluated by liquid chromatography using the compound shown below (hexobarbital). The column performance (t value, Rs value, N value) of an optical isomer separation column using a packing material (supported amount 8.0% based on HAS assay in reaction filtrate by Bradford method) comprising human serum albumin (HAS) chemically bonded to completely porous silica gel (particle size 5 µm, pore diameter 12 nm) by the methods described in Example 8 was also given as Comparative Example 5. For the evaluation conditions, 10 mM aqueous ammonium acetate solution (pH 7.0)/2-propanol=95/5 was used as the mobile phase, with a flow rate of 0.10 mL/min and the temperature set at 25° C. in both Example 8 and Comparative Example 5.

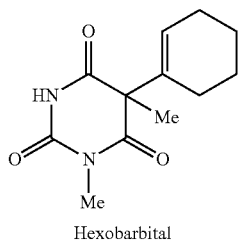

Hexobarbital

TABLE 5

| | Separating agent | |
|---|---|---|
| Racemate | Example 8: Core-shell, carrying rate 3.5 wt % | Comparative Example 5: Completely porous, supported amount 8.0 wt % |
| Hexobarbital | t1 = 5.125<br>t2 = 6.982<br>N1 = 363<br>N2 = 355<br>α = 3.008 | t1 = 6.500<br>t2 = 8.408<br>N1 = 288<br>N2 = 294<br>α = 1.984 |

The invention claimed is:

1. A separating agent comprising a carrier and a ligand fixed on a surface of a carrier by chemical bonding, wherein the carrier is a core-shell particle formed of a non-porous core and a porous shell, the shell having a pore diameter of 9 nm or more and formed of a hydrolysate of polyalkoxysiloxane, and the ligand is an optically active polymer, optically inactive polyester, protein, nucleic acid, or optically active organic compound with a molecular weight of 50 to 1000.

2. The separating agent according to claim 1, wherein the core of the core-shell particle is formed of an inorganic material, and a ratio of the thicknesses of the core and the shell is from 4:1 to 2:1.

3. The separating agent according to claim 1, wherein the optically active polymer is selected from polysaccharides or derivatives thereof, optically active poly(meth)acrylic acid amides, optically active polyamino acids and optically active polyamides.

4. The separating agent according to claim 1, wherein the protein is selected from protein A, protein G, protein L, albumin and functional variants thereof.

5. The separating agent according to claim 1, wherein the optically inactive polyester is selected from polyethylene terephthalate, polybutylene terephthalate and polyactic acid.

6. The separating agent according to claim 1, wherein the nucleic acid is selected from DNA and RNA with 5 to 10000 bases, and derivatives thereof.

7. The separating agent according to claim 1, wherein the optically active organic compound with a molecular weight of 50 to 1000 is selected from compounds having binaphthyl structures and crown ether-like cyclic structures, N-acylated amino acids, N-carbamoyl amino acids, and N-carbamoyl-α-aromatic alkylamines.

8. The separating agent according to claim 1, wherein the separating agent is a separating agent for chromatography.

* * * * *